United States Patent
Schreck et al.

(12) United States Patent (10) Patent No.: US 6,952,097 B2
(45) Date of Patent: Oct. 4, 2005

(54) METHOD FOR SLICE POSITION PLANNING OF TOMOGRAPHIC MEASUREMENTS, USING STATISTICAL IMAGES

(75) Inventors: Oliver Schreck, Bamberg (DE); Mike Müller, Möhrendorf (DE); Martin Harder, Nürnberg (DE); Hans-Peter Hollenbach, Eggolsheim (DE); Franz Schmitt, Somerville, MA (US); Ines Nimsky, Erlangen (DE); Anders Dale, Boston, MA (US); Andre Van Der Kouwe, Woburn, MA (US)

(73) Assignee: Siemens Aktiengesellschaft, Munich (DE)

( * ) Notice: Subject to any disclaimer, the term of this patent is extended or adjusted under 35 U.S.C. 154(b) by 61 days.

(21) Appl. No.: 10/691,405

(22) Filed: Oct. 22, 2003

(65) Prior Publication Data

US 2005/0088177 A1 Apr. 28, 2005

(51) Int. Cl.$^7$ ................................................ G01V 3/00
(52) U.S. Cl. ...................................... 324/309; 324/410
(58) Field of Search ................................ 324/309, 306, 324/307, 300; 600/410, 411, 416, 417, 424

(56) References Cited

U.S. PATENT DOCUMENTS

| | | | |
|---|---|---|---|
| 5,231,651 A | | 7/1993 | Ozaki et al. |
| 5,398,684 A | * | 3/1995 | Hardy ........................ 600/391 |
| 5,512,827 A | * | 4/1996 | Hardy et al. ................. 600/410 |
| 6,195,409 B1 | | 2/2001 | Chang et al. |
| 6,275,035 B1 | * | 8/2001 | Debbins et al. ............. 324/307 |
| 6,348,793 B1 | * | 2/2002 | Balloni et al. .............. 324/309 |
| 2002/0087061 A1 | | 7/2002 | Lifshitz et al. |
| 2002/0172408 A1 | | 11/2002 | Saito et al. |
| 2003/0139659 A1 | | 7/2003 | Anders et al. |

FOREIGN PATENT DOCUMENTS

| | | |
|---|---|---|
| WO | WO 01/59708 | 8/2001 |
| WO | WO 02/43003 | 5/2002 |
| WO | WO 02/098292 | 12/2002 |

* cited by examiner

*Primary Examiner*—Louis Arana
(74) *Attorney, Agent, or Firm*—Schiff Hardin LLP (57) ABSTRACT

In a method and computer program product for operating a tomographic imaging apparatus, a standard measurement protocol is generated by displaying a planning representation of a standard object, defining a spatial position of a standard imaging area in the planning representation, and storing, as the standard measurement protocol for the standard object, a reference to the standard object and parameters of the standard imaging area. Such a standard measurement protocol can then be used in the slice position planning for an actual tomographic measurement, by obtaining data representing features of an examination object, corresponding to the standard object, determining a geometrical relation of the features of the examination object to features of the standard object, and generating an object-specific measurement protocol wherein the imaging area is positioned relative to the examination object by modification of the standard measurement protocol.

23 Claims, 5 Drawing Sheets

METHOD FOR SLICE POSITION PLANNING OF TOMOGRAPHIC MEASUREMENTS, USING STATISTICAL IMAGES

The subject matter claimed in this application was made with the assistance of United States government funding (NIH Grants NIH-NIBIB 1R01EB00790-01, NIH-NIBIB 8R01EB00307-05, NIH NCRR 5P41RR14075-04). The United States government has certain rights in this invention.

BACKGROUND OF THE INVENTION

1. Field of the Invention

The present invention is directed to a method for slice position planning of tomographic (magnetic resonance) measurements, including a protocol for operating a magnetic resonance imaging apparatus.

2. Description of the Prior Art

Magnetic resonance imaging (MRI, also known as magnetic resonance tomography (MRT)) is based on the physical phenomenon of nuclear magnetic resonance and has been successfully utilized as an imaging modality in medicine and in biophysics for more than fifteen years. In this imaging modality, a subject, such as a living patient, is subjected to a strong, constant magnetic field. As a result, the nuclear spins of the atoms in the subject, that were previously irregularly oriented, are aligned. Radio-frequency energy emitted into the subject then excites these "ordered" nuclear spins to a specific resonance. This resonance generates the actual measurement signal, which is received with suitable reception coils. By utilizing non-uniform magnetic fields (gradient fields) generated by gradient coils, the signals received from the examination subject can be spatially encoded in all three spatial directions. A slice of the examination subject for which an image is to be generated can be freely selected, thereby allowing tomograms of the human body to be obtained in all orientations. Magnetic resonance imaging as a tomographic method for medical diagnostic purposes is primarily distinguished as a "non-invasive" examination technique with versatile contrast capability. Due to the excellent presentation of soft tissue, magnetic resonance imaging has developed into an imaging modality that is often superior to x-ray computed tomography (CT). Magnetic resonance imaging is currently based on the use of spin echo sequences and gradient echo sequences that enable an excellent image quality to be obtained, with measurement times on the order of magnitude of minutes.

Each examination (scan) of a subject in a particular magnetic resonance imaging installation must be planned in advance. The planning involves selection of the type of pulse sequence, as well as the selection or designation of many individual parameters of the selected pulse sequence. The selection of the pulse sequence and the parameterization thereof are, in turn, based on many variables that differ from scan-to-scan. Such variables are related to the specific patient, the type of imaging installation, and the particular type and orientation of the magnetic resonance image that is desired to be obtained. The image to be obtained is dependent not only on anatomical factors, but also on the particular pathological condition, or suspected pathological condition, that is being investigated.

For clinical MR scanners, protocols are predefined with regard to slice positioning, but such protocols are not based on the actual positioning of the patient in the scanner for the particular examination to be undertaken. Usually, the protocols are defined relative to the center of the origin of the basic field magnet, which usually also is the origin of the imaging volume, and straightforward axial, sagittal or coronal slices are selected depending on the preferred protocol orientation. For performing the actual scan, the final slice position must be adjusted manually, otherwise the slice will not coincide with the desired body region of the subject. In principle, this manual procedure must be performed with regard to every protocol and every patient. This not only prolongs the time that the patient must spend in the scanner, which is discomforting to the patient, but also slows the patient throughput (i.e., results in a smaller number of patients being scanned within a given time than would be possible without such manual positioning).

Conventionally, such manual re-alignment of the slices for the actual scan, compared to the slice alignment in the predefined protocol requires the use of a so-called localizer protocol. This involves positioning the patient in the scanner, undertaking a localizer scan, position the slices for the actual diagnostic scan based on the images obtained in the localizer scan, and undertaking the clinical or diagnostic scan from which diagnostic images will be obtained.

In the context of conventional slice position planning, the use of templates is described in U.S. Pat. No. 6,195,409, and the processing of medical images employing techniques suitable for slice position planning is described in PCT Application WO 02/43003. The mapping of a particular property in the context of image processing is disclosed in PCT Application WO 02/098292, and the registration of object views is described in PCT Application WO 01/59708.

SUMMARY OF THE INVENTION

It is an object of the present invention to provide a method for slice position planning of tomographic measurements which avoids the above-described manual slice re-alignment. A further object of the present invention is to provide such a method which avoids the need for a localizer protocol of the type described above. This object is achieved in accordance with the principles of the present invention in a method for slice position planning of MR measurements wherein, instead of planning the slices for each individual patient for each individual scan, the slice or slices for a particular scan is/are planned using a statistical dataset which represents the geometrical details of the organ of interest in the scan. The statistical dataset represents a "standard" image of the organ of interest. The dataset can be obtained from a standard organ atlas, many of which are known and accessible, or can be produced from a data acquisition system by averaging several measured datasets that have previously been obtained from other patients, and that have been stored. The statistical dataset, or atlas, is displayed as a planning representation in a global slice-positioning environment. The measurement for an imaging area (geometrical parameters, sequence parameters, etc.) is planned using this statistical dataset, and is stored as a standard measurement protocol for the particular "standard" human organ in question. The standard measurement protocol includes information regarding, for example, the position of the imaging area in the dataset and the position of the imaging area regarding the "standard" human organ. The standard measurement protocol also includes information as to the number of slices, the orientation of the slices, the number of pixels per slice, the size of the pixels, etc. in the imaging area. The standard measurement protocol may allow the measurement of a series of imaging areas and/or may contain information regarding saturation areas, etc.

Such standard measurement protocols can be respectively generated for different types of scans, for example, for a brain scan, a scan of the pituitary gland, and fMRI scan, a scan for epilepsy, a scan of the optical nerves, or a scan of the acoustic nerves.

To be able to use the standard measurement protocol to examine (scan) an individual patient, the protocol has to be adjusted or modified to produce a patient-specific measurement protocol. For this purpose, the organ of the patient for which an image is to be obtained is localized in the data acquisition system (scanner) by a first low-resolution measurement, such as using a 3D localizer or auto align sequence, and a geometrical mapping of the organ is then undertaken. For this mapping the geometrical relation of the standard (statistical) organ to the organ of the patient must be determined. This can be accomplished by comparing templates, or by a correlation of the corresponding datasets. As a result, a transformation matrix is developed, that defines how to rotate, translate, expand or shrink the image of the patient organ so as to map it with the standard organ. The position of the imaging area (slicebox) of the standard measurement protocol is adjusted according to the transformation matrix. This results in the patient-specific measurement protocol.

A significant advantage of the inventive method is the high degree of reproducibility that can be obtained in the examination. Because the imaging area is each time automatically determined by starting from the standard image area, that is adjusted according to the actual anatomical features of the patient (that in general do not change), the same patient can be scanned a number of times, separated by relatively long time durations, so that the respective images from the time-separated scans can be compared in a meaningful manner. This is particularly advantageous when the scans are for the purpose of following up treatment for a particular pathological condition, such as monitoring the size of a cancerous tumor during the course of radiation therapy or chemotherapy. When a patient is scanned at times that are separated from each other, it sometimes can be difficult to compare the images obtained from the respective scans because it cannot be reliably determined that changes in the images detected as a result of the comparison have occurred because of an actual change in the size of the tumor, or because the orientation of the slice in one of the images was not identical to the orientation of the slice in the other of the images. Because of the high degree of reproducibility achieved with the inventive procedure, when changes are detected between time-separated images, it can be more reliably assumed that those changes represent actual anatomical changes, rather than changes resulting from inconsistent slice positioning.

A further advantage obtained with the inventive method is a higher patient throughput with regard to the imaging installation, achieved by the significant decrease in time for planning each tomographic measurement.

Although the inventive method has been described above, and is described in more detail below, in the context of magnetic resonance imaging, the inventive method can be used in any type of tomographic imaging modality, including computed tomography and ultrasound, for example.

DESCRIPTION OF THE PREFERRED EMBODIMENTS

Figure 1:
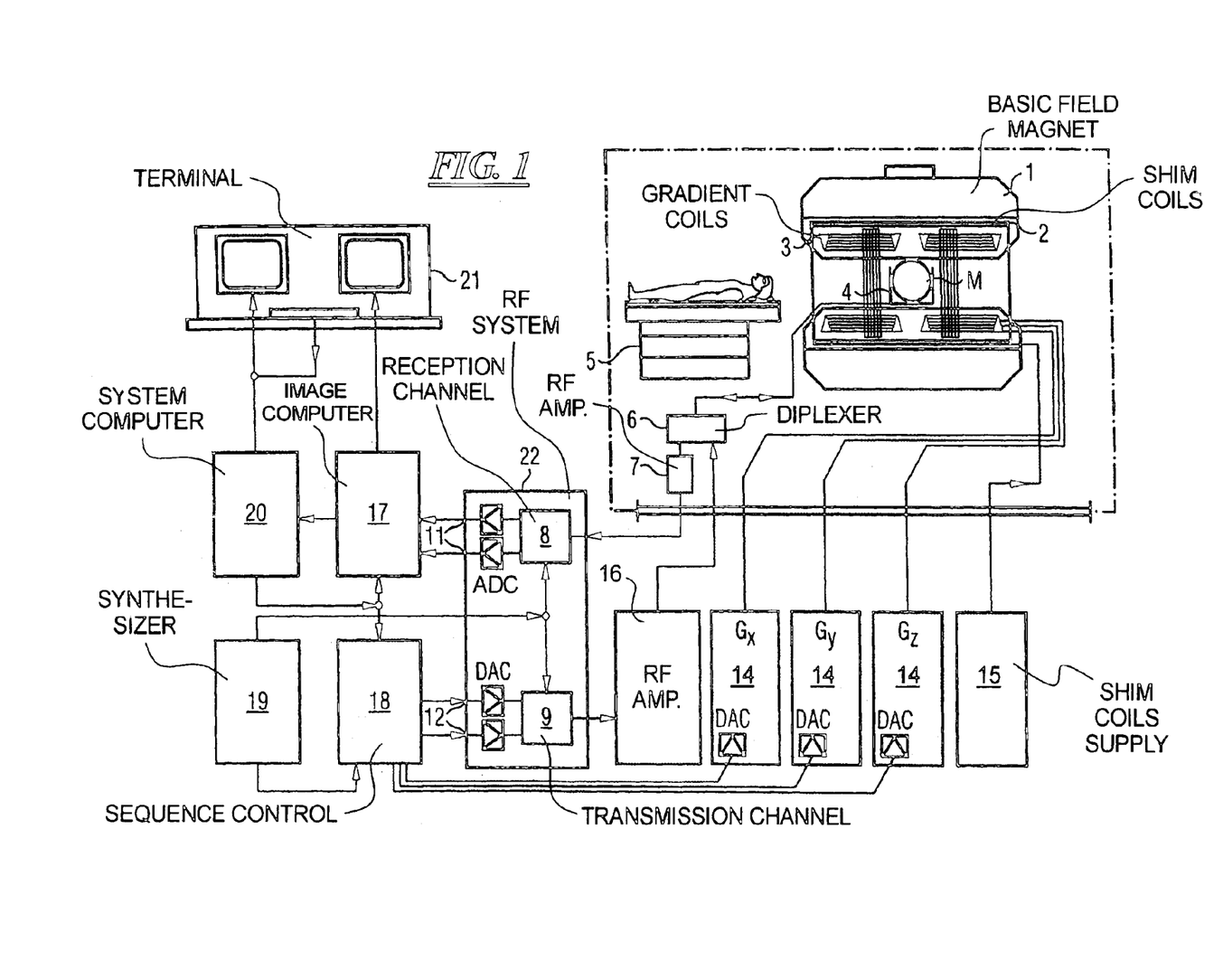
FIG. 1 is a schematic block diagram of a magnetic resonance imaging apparatus, used an exemplary tomographic imaging modality for explaining the inventive method.

FIG. 1 schematically illustrates a magnetic resonance imaging (tomography) apparatus for generating a magnetic resonance image of a subject, as an example of a tomographic imaging modality operable according to the present invention. The components of the nuclear magnetic resonance tomography apparatus correspond to those of a conventional tomography apparatus, but it is controlled according to the invention. A basic field magnet 1 generates a time-constant, intense magnetic field for polarization (alignment) of the nuclear spins in the examination region of a subject such as, for example, a part of a human body to be examined. The high homogeneity of the basic magnetic field required for the nuclear magnetic resonance measurement is defined in a spherical measurement volume M in which the part of the human body to be examined is introduced. For supporting the homogeneity demands and, in particular, for eliminating time-invariable influences, shim plates of ferromagnetic material are attached at suitable locations. Time-variable influences are eliminated by shim coils 2 that are driven by a shim power supply 15.

A cylindrical gradient coil system 3 is built into the basic field magnet 1, the system 3 being composed of three sub-windings. Each sub-winding is supplied with current by an amplifier 14 for generating a linear gradient field in the respective directions of a Cartesian coordinate system. The first, sub-winding of the gradient field system 3 generates a gradient $G_x$ in the x-direction, the second sub-winding generates a gradient $G_y$ in the y-direction, and the third sub-winding generates a gradient $G_z$ in the z-direction. Each amplifier 14 has a digital-to-analog converter DAC that is driven by a sequence control 18 for the time-controlled generation of gradient pulses.

A radio-frequency antenna 4 is situated within the gradient field system 3. The antenna 4 converts the radio-frequency pulses emitted by a radio-frequency power amplifier into an alternating magnetic field for exciting the nuclei and aligning the nuclear spins of the subject under examination, or of a region of the subject under examination. The radio-frequency antenna 4 is composed of one or more RF transmission coils and a number of RF reception coils in the form of an arrangement (preferably linear) of component coils. The alternating field proceeding from the processing nuclear spins, i.e. the nuclear spin echo signals produced as a rule by a pulse sequence composed of one or more radio-frequency pulses and one or more gradient pulses, is also converted into a voltage by the RF reception coils of the radio-frequency antenna 4, this voltage being supplied via an amplifier 7 to a radio-frequency reception channel 8 of a radio-frequency system 22. The radio-frequency system 22 also has a transmission channel 9 wherein the radio-frequency pulses are generated for exciting magnetic nuclear resonance. The respective radio-frequency pulses are digitally presented as a sequence of complex numbers on the basis of a pulse sequence in the sequence control 18 prescribed by the system computer 20. This number sequence—as a real part and an imaginary part—is supplied via respective inputs 12 to a digital-to-analog converter DAC in the radio-frequency system 22 and is supplied from there to a transmission channel 9. In the transmission channel 9, the pulse sequences are modulated onto a radio-frequency carrier signal having a basic frequency corresponding to the resonant frequency of the nuclear spins in the measurement volume.

The switching from transmission mode to reception mode ensues via a transmission/reception diplexer 6. The RF transmission coil of the radio-frequency antenna 4 radiates the radio-frequency pulses, based on signals from a radio-frequency power amplifier 16, for excitation of the nuclear spins into the measurement volume M and samples the resulting echo signals via the RF reception coils. The acquired nuclear magnetic resonance signals are phase-sensitively demodulated in the reception channel 8 of the radio-frequency system 22 and are converted via respective analog-to-digital converters ADC into the real part and the imaginary part of the measured signal, which are respectively supplied to outputs 11. An image computer 17 reconstructs an image from the measured data acquired in this way. Administration of the measured data, the image data and the control programs ensues via the system computer 20. On the basis of control programs, the sequence control 18 monitors the generation of the respectively desired pulse sequences and the corresponding sampling of k-space. In particular, the sequence control 18 controls the timed switching of the gradients, the emission of the radio-frequency pulses with defined phase and amplitude, as well as the reception of the nuclear magnetic resonance signals. The timing signals for the radio-frequency system 22 and the sequence control 18 is made available by a synthesizer 19. The selection of corresponding control programs for generating a nuclear magnetic resonance image as well as the presentation of the generated nuclear magnetic resonance image ensues via a terminal 21 that has a keyboard as well as one or more picture screens.

The inventive method can be executed using the terminal 21 and the system computer 20. For executing the method illustrated in the flowchart of FIG. 2, the system computer 20 can either have stored therein, or have access to, an atlas of anatomical organs. A number of such atlases are commercially available and/or accessible on-line. Such an atlas contains a statistical dataset for each of a number of different anatomical organs.

For the purpose of planning a scan, the atlas or statistical dataset of the organ which will be imaged in the scan is loaded, accessed or retrieved and the particular field of interest in the scan is designated. The imaging area is then designed, and the relevant parameters that have been entered are stored together with a reference to the atlas that was employed in producing this standard measurement protocol.

Figure 2:
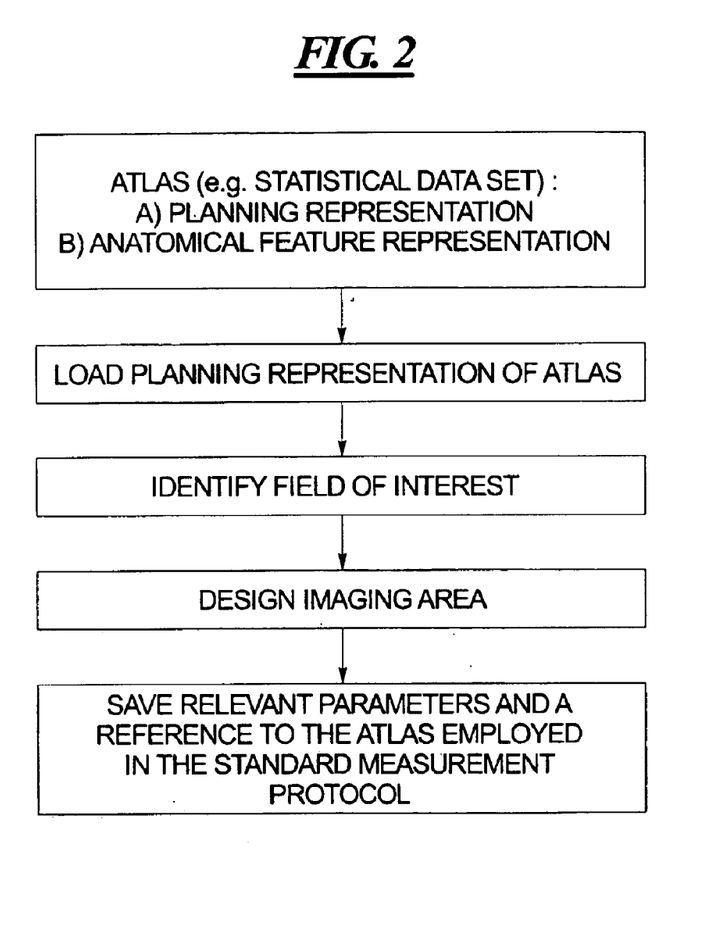
FIG. 2 is a flowchart of the basic steps for generating a standard measurement protocol in accordance with the invention.
Figure 3:
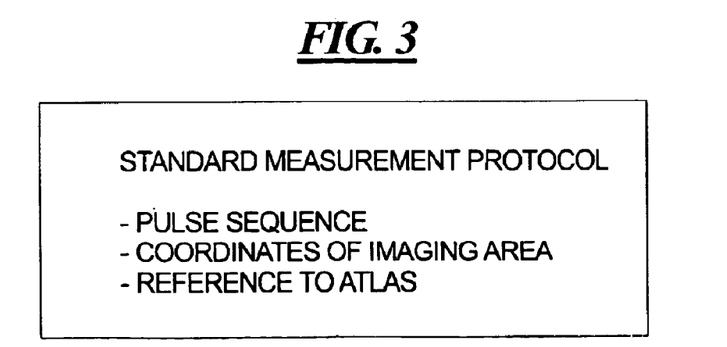
FIG. 3 illustrates the basic components or content of the standard measurement protocol in accordance with the invention.

The basic contents of the standard measurement protocol for each type of scan that is developed according to the flowchart shown in FIG. 2 are presented in FIG. 3. These components include the pulse sequence that will be used in the scan, the coordinates of the imaging area, and a reference to the atlas that was used in producing the protocol.

The region in which the slice or slices in the scan will be obtained is known as the "slicebox." The orientation of the slicebox for a number of different standard measurement protocols produced in accordance with the invention are shown with reference to a standard head in FIGS. 4 through 9.

Figure 4:
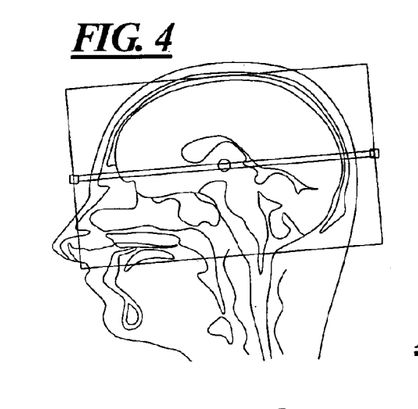
FIG. 4 illustrates the positioning of the slicebox relative to a standard head in a standard measurement protocol produced in accordance with the invention for a brain scan (brain standard).
Figure 5:
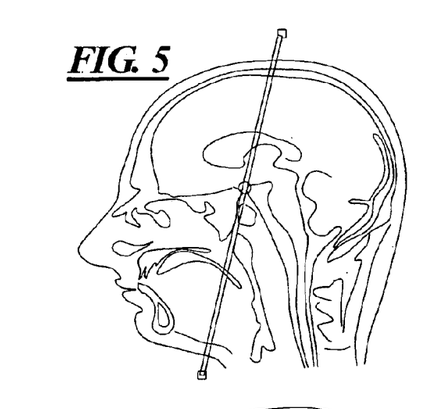
FIG. 5 illustrates the positioning of the slicebox relative to a standard head in a standard measurement protocol produced in accordance with the invention for a pituitary gland scan (pituitary standard).
Figure 6:
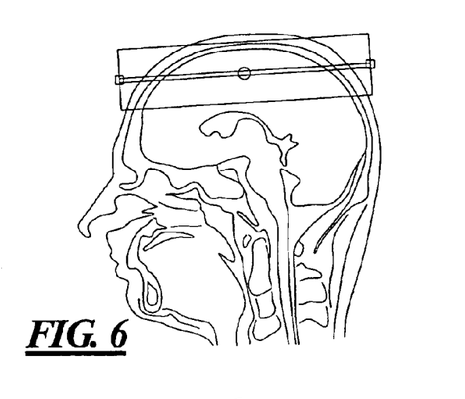
FIG. 6 illustrates the positioning of the slicebox relative to a standard head in a standard measurement protocol produced in accordance with the invention for a fMRI scan (fMRI standard).

FIG. 4 illustrates the orientation of the slicebox relative to the standard head (head atlas) for a brain scan (brain standard). FIG. 5 shows the orientation of the slicebox for a scan of the pituitary gland (pituitary standard). FIG. 6 shows the orientation of the slicebox for functional magnetic resonance imaging (fMRI standard). In a functional magnetic resonance imaging scan, the subject is periodically stimulated, such as by a flashing light, and brain activity is detected by monitoring the increased oxygen consumption that occurs in the portion of the brain wherein activity is caused by the stimulation.

Figure 7:
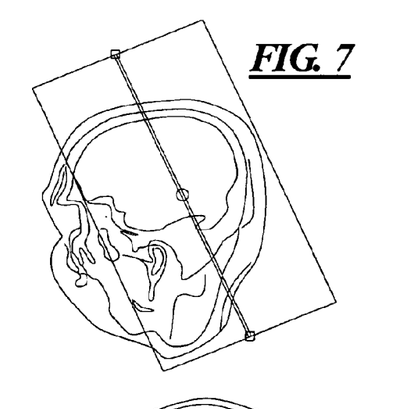
FIG. 7 illustrates the positioning of the slicebox relative to a standard head in a standard measurement protocol produced in accordance with the invention for a epilepsy scan (epilepsy standard).
Figures 8, 9:
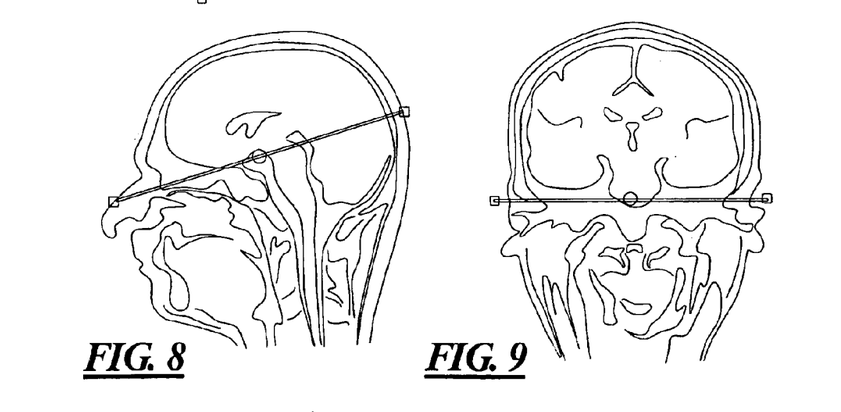
FIG. 8 illustrates the positioning of the slicebox relative to a standard head in a standard measurement protocol produced in accordance with the invention for a optic nerve scan (optic nerve standard).
FIG. 9 illustrates the positioning of the slicebox relative to a standard head in a standard measurement protocol produced in accordance with the invention for a acoustic nerve scan (acoustic nerve standard).

FIG. 7 illustrates the orientation of the slicebox relative to the standard head for a scan to detect symptoms in the brain indicative of epilepsy (epilepsy standard). FIG. 8 illustrates the orientation of the slicebox (here, as in FIG. 5, a single slice) for a scan of the optic nerves (optic nerve standard) and FIG. 9 illustrates the slicebox for a scan of the auditory nerves (auditory nerve standard).

Figure 10:
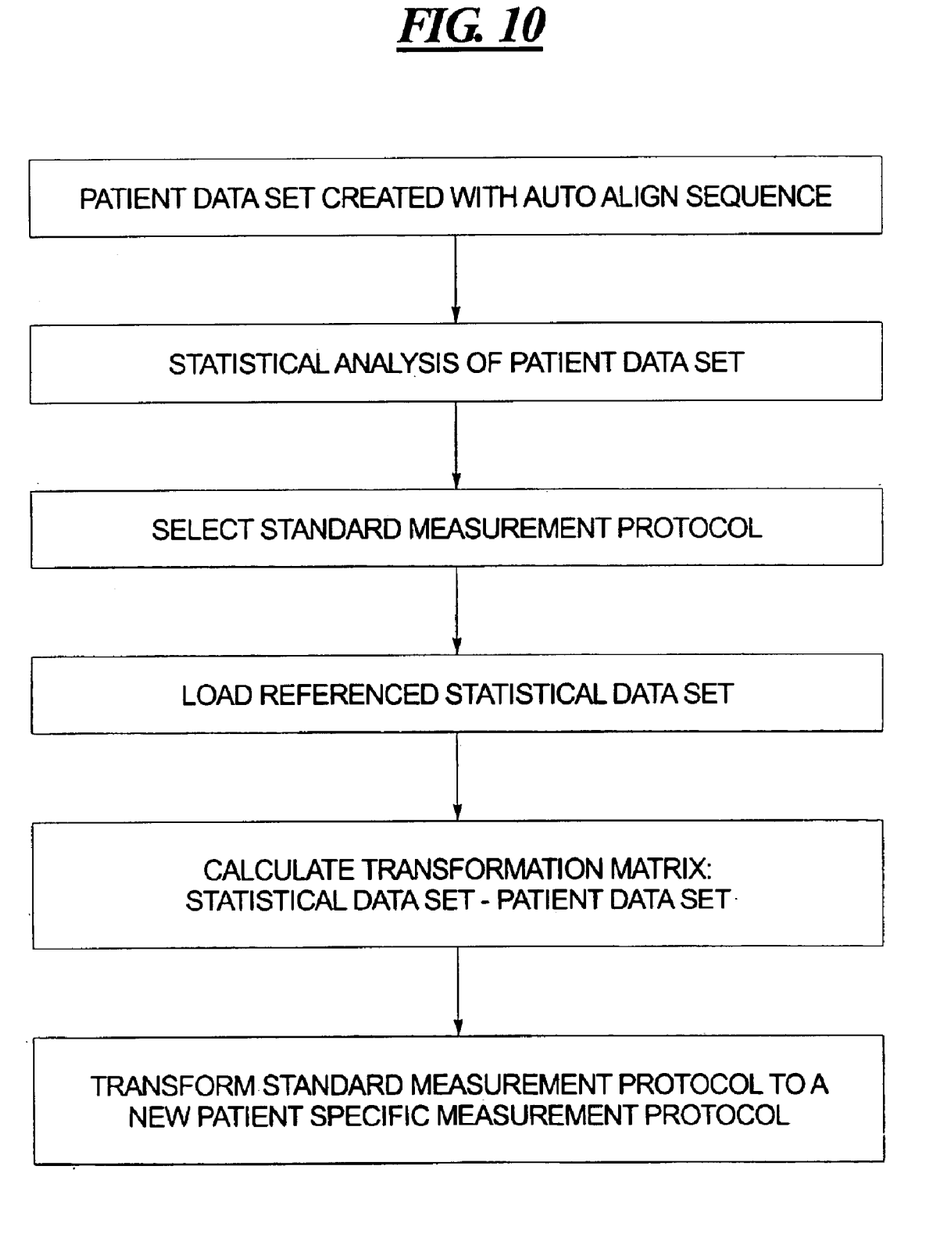
FIG. 10 is a flowchart of the inventive method for producing a patient-specific measurement protocol.

The production of such standard measurement protocols for different organs in accordance with the invention has "stand alone" utility, and can be used for other purposes. Further in accordance with the present invention, however, the standard measurement protocol is used in the method illustrated in FIG. 10 for producing a patient-specific measurement protocol. As illustrated in FIG. 10, a patient dataset is created with an auto align sequence, which represents the actual position of the patient in the scanner for a particular examination. The patient dataset is statistically analyzed, and the appropriate standard measurement protocol, for among the standard measurement protocols generated as described above, is selected. The statistical dataset (atlas) that is referenced in the selected standard measurement protocol is then loaded (or accessed or retrieved). A transformation matrix is then calculated which provides a mapping between the statistical dataset and the patient dataset. The standard measurement protocol is then transformed or converted, using the transformation matrix, to a patient-specific measurement protocol for the particular patient and the particular scan.

Figure 11A:
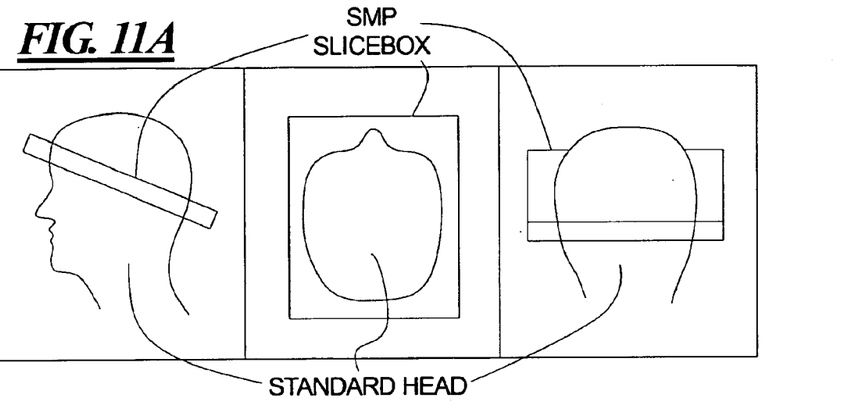
FIGS. 11A, 11B and 11C are exemplary illustrations for explaining the inventive method of FIG. 10.
Figure 11B:
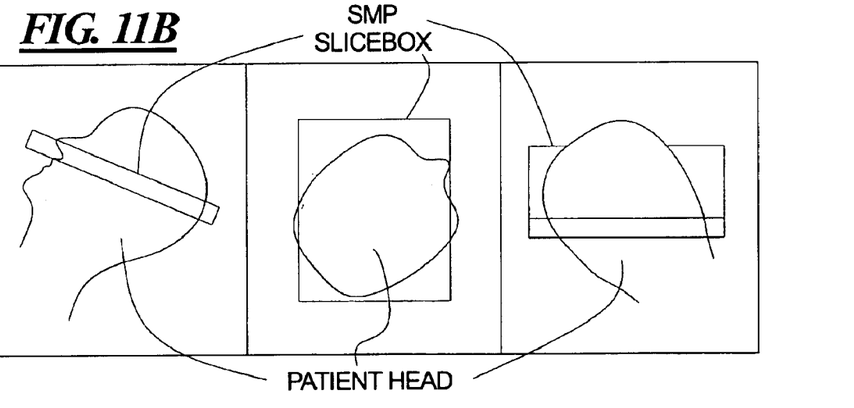
Figure 11C:
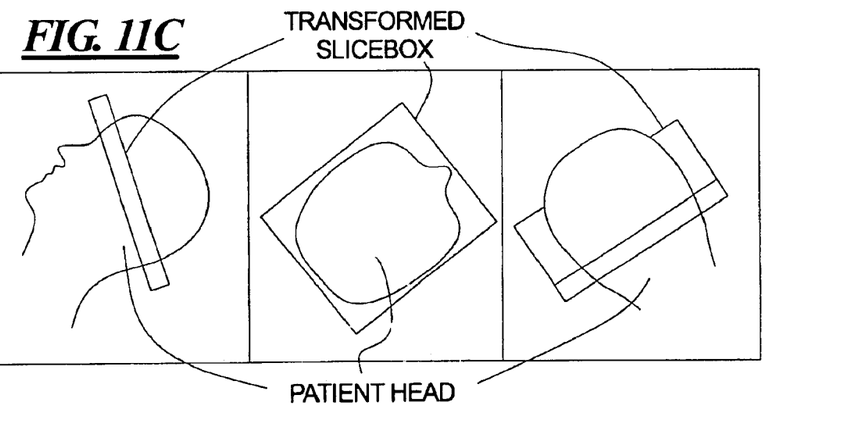

The procedure set forth in the flowchart of FIG. 10 is illustrated in the sequence shown in FIGS. 11A, 11B and 11C. The illustrations that are schematically shown in FIGS. 11A, 11B and 11C may be visually displayed at the screen of the terminal 21, if desired, however, since it is not critical for the operator to actually view these representations, FIGS.

11A, 11B and 11C can be considered as schematic illustrations of the data manipulations that are taking place in the computer during the execution of the inventive method.

FIG. 11A shows a standard head (head atlas) in three different views with the standard measurement protocol (SMP) slicebox indicated relative to the standard head. This representation can correspond to any of the examples shown in FIGS. 4 through 9, or a standard measurement protocol for some other organ.

FIG. 11B shows the same views of the head, but these views are obtained from the low-resolution scan of the actual patient in the scanning apparatus. The orientation of the organ of interest, in this case the patient head, will almost certainly be different from the orientation of the standard head shown in FIG. 11A. The SMP slicebox, however, is shown in each view in a position that is identical to the slice box position in FIG. 11A. Since the actual position of the patient head is different from the position of the standard head, the SMP slicebox would not be properly oriented relative to the actual patient head for conducting the desired scan.

In order to restore the proper orientation between the patient head and the slicebox, the aforementioned transformation matrix is generated, which represents a mapping between the standard head and the patient head. The data representing the SMP slicebox in FIG. 11B are then operated on by the transformation matrix, thereby producing a transformed slicebox shown in FIG. 11C. This transformed slicebox has the same orientation relative to the patient head as the SMP slicebox has relative to the standard head.

FIG. 11C therefore represents the resulting patient specific measurement protocol at the end of the flowchart in FIG. 10. The actual diagnostic scan can then be conducted using this patient-specific measurement protocol.

As noted above, although the inventive procedure has been explained in the context of magnetic resonance imaging, it can be used with similar benefit in other types of tomographic imaging, such as computed tomography and ultrasound.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for creating a standard measurement protocol for a tomographic imaging system, comprising the steps of:
   at a computerized interface with which an operator can interact, compiling a planning representation of a standard anatomical subject, having anatomical features, as a statistical average of a plurality of actual objects in respective patients each corresponding to said standard anatomical object, and displaying said planning representation of said standard anatomical object including said anatomical features;
   by interacting through said interface with the displayed planning representation, defining a spatial position, relative to said standard anatomical object, of a standard tomographic imaging area in said planning representation; and
   generating and storing a standard measurement protocol comprising parameters associated with said standard imaging area and a reference that designates said standard anatomical object.

2. A method as claimed in claim 1 wherein the step of generating and storing said standard measurement protocol comprises storing parameters that define said spatial position of said standard imaging area.

3. A method as claimed in claim 1 wherein the step of generating and storing a standard measurement protocol further comprises including in said standard measurement protocol parameters for operating said tomographic imaging system to obtain an image, within said standard imaging area, of a portion of a patient, corresponding to said standard anatomical object, in said tomographic imaging system.

4. A method as claimed in claim 1 wherein said tomographic imaging system is a magnetic resonance imaging apparatus, and wherein the step of generating and storing a standard measurement protocol further comprises including designation of a pulse sequence for said magnetic resonance imaging apparatus for obtaining an image, within said standard imaging area, of a portion of a patient, corresponding to said standard anatomical object, in said magnetic resonance imaging apparatus.

5. A method as claimed in claim 1 comprising displaying geometrical features of said standard anatomical subject as said anatomical features.

6. A method for planning positioning of an imaging area in an actual object in a tomographic imaging system, comprising the steps of:
   placing said actual object patient in said tomographic imaging system and obtaining data representing features of said actual object using said tomographic imaging system;
   making a standard measurement protocol available to a computer and in said standard measurement protocol in said computer, consulting an atlas to obtain a standard anatomical object, said standard measurement protocol defining a spatial position of a standard imaging area with reference to a standard object, said standard measurement protocol referencing a dataset representing features of said standard object;
   in said computer, determining a geometrical relation between said features of said actual object patient and said features of said standard object, from said dataset representing said features of said actual object and said dataset representing said features of said standard object;
   creating an actual object-specific measurement protocol, wherein said imaging area is positioned relative to said actual object, by modifying said standard measurement protocol dependent on said geometrical relation; and
   using said object-specific measurement protocol to obtain an image of said actual object within said image area in said tomographic imaging system.

7. A method as claimed in claim 6 wherein said actual object is a patient and wherein said standard object is a standard anatomical object, and wherein said features represented by the respective datasets are anatomical features.

8. A method as claimed in claim 6 wherein the step of modifying said standard measurement protocol to create said object-specific measurement protocol comprises positioning said imaging area relative to said actual object identically to a position of said standard imaging area relative to said standard object.

9. A method as claimed in claim 6 comprising, within said standard measurement protocol, defining respective spatial positions for a variety of standard imaging areas with reference to said standard object.

10. A method as claimed in claim 9 comprising obtaining a variety of images of said actual object using said object-specific measurement protocol, corresponding to said variety of standard imaging areas.

11. A method as claimed in claim 6 comprising generating said geometrical relation by correlating said dataset representing features of said patient and said dataset representing anatomical features of said standard anatomical object.

12. A method as claimed in claim 6 comprising, in said standard measurement protocol, defining a position and size of said standard imaging area.

13. A method as claimed in claim 6 comprising, in said standard measurement protocol, defining a number and thickness of image slices in said standard imaging area.

14. A method as claimed in claim 6 wherein said tomographic imaging system is a magnetic resonance system, and comprising including a pulse sequence, in said standard measurement protocol, for operating said magnetic resonance apparatus using said patient-specific measurement protocol.

15. A method for planning positioning of an imaging area of a patient in a tomographical imaging system, comprising:

placing said patient in said tomographic imaging system and obtaining data representing anatomical features of said patient using said tomographic imaging system;

making a standard measurement protocol available to a computer and in said standard measurement protocol in said computer, compiling a standard anatomical object as a statistical compilation of data from a plurality of actual objects of respective patients each corresponding to said standard anatomical object;

in said computer, determining a geometrical relation between said anatomical features of said patient and said anatomical features of said standard anatomical object, from said dataset representing said anatomical features of said patient and said dataset representing said anatomical feature of said standard anatomical object;

creating an actual object-specific measurement protocol, wherein said imaging area is positioned relative to said patient, by modifying said standard measurement protocol dependent on said geometrical relation; and using said object-specific measurement protocol to obtain an image of said patient within said image area in said tomographic imaging system.

16. A method as claimed in claim 15 comprising generating said standard anatomical object in said standard measurement protocol as an average of said plurality of actual objects of respective patients.

17. A method as claimed in claim 15 wherein the step of modifying said standard measurement protocol to create said object-specific measurement protocol comprises positioning said imaging area relative to said patient identically to a position of said standard imaging area relative to said standard anatomical object.

18. A method as claimed in claim 15 comprising, within said standard measurement protocol, defining respective spatial positions for a variety of standard imaging areas with reference to said standard anatomical object.

19. A method as claimed in claim 18 comprising obtaining a variety of images of said patient using said object-specific measurement protocol, corresponding to said variety of standard imaging areas.

20. A method as claimed in claim 15 comprising generating said geometrical relation by correlating said dataset representing features of said patient and said dataset representing anatomical features of said standard anatomical object.

21. A method as claimed in claim 15 comprising, in said standard measurement protocol, defining a position and size of said standard imaging area.

22. A method as claimed in claim 15 comprising, in said standard measurement protocol, defining a number and thickness of image slices in said standard imaging area.

23. A method as claimed in claim 15 wherein said tomographic imaging system is a magnetic resonance system, and comprising including a pulse sequence, in said standard measurement protocol, for operating said magnetic resonance apparatus using said patient-specific measurement protocol.

* * * * *